US00PP34851P2

(12) United States Plant Patent
van Geest

(10) Patent No.: US PP34,851 P2
(45) Date of Patent: Dec. 20, 2022

(54) ***FICUS* PLANT NAMED 'ESPE2007'**

(50) Latin Name: ***Ficus cyathistipula* Warb.**
Varietal Denomination: 'ESPE2007'

(71) Applicant: J. Van Geest Holding B.V., 's Gravenzande (NL)

(72) Inventor: Jan van Geest, 's Gravenzande (NL)

(73) Assignee: J. Van Geest Holding B.V., 's Gravenzande (NL)

( * ) Notice: Subject to any disclaimer, the term of this patent is extended or adjusted under 35 U.S.C. 154(b) by 0 days.

(21) Appl. No.: 17/803,540

(22) Filed: Aug. 17, 2022

(51) Int. Cl.
*A01H 5/12* (2018.01)

(52) U.S. Cl.
USPC ..... Plt./211

(58) Field of Classification Search
USPC ..... Plt./211
See application file for complete search history.

*Primary Examiner* — Annette H Para
(74) *Attorney, Agent, or Firm* — Samuel R. McCoy, Jr.

(57) ABSTRACT

A new and distinct variety of *Ficus cyathistipula* plant named 'ESPE2007' which is characterized by the combination of a compact growth habit with a relatively fast rate of growth which makes it suited to production and sale in small container sizes, small leaves, prominent stipules, and the stability of all characteristics from generation to generation.

3 Drawing Sheets

Latin name of the genus and species: The Latin name of the genus and species of the novel variety disclosed herein is *Ficus cyathistipula* Warb.

Variety denomination: The inventive variety of *Ficus* disclosed herein has been given the variety denomination 'ESPE2007'.

BACKGROUND OF THE INVENTION

Parentage: 'ESPE2007' originated as a naturally occurring, whole-plant mutation of an unnamed *Ficus cyathistipula* plant (not patented). The inventor regularly discovers mutations of *Ficus cyathistipula* at his commercial greenhouse in 's-Gravenzande, the Netherlands and, as a result, a selection program was established with the goal of developing a new cultivar that would be more compact and suitable for production and sale in smaller container sizes. From 2017 through early 2018, more than 30 mutations were discovered and subsequently isolated for further observation. Each mutation was asexually propagated on three separate occasions and grown to maturity, in order to confirm the distinctness and stability of the characteristics first observed. In September of 2018, the candidate variety was ultimately selected from the 30 candidates due its compact growth habit, smaller leaves, and fast rate of growth which made it suitable for production in smaller container sizes, ranging from 14 to 21 centimeters.

Asexual Reproduction: Asexual reproduction of ESPE2007', by way of stem cuttings, was first initiated in 2018 at a commercial greenhouse in 's-Gravenzande, the Netherlands. Through three subsequent generations, the unique features of this cultivar have proven to be stable and true to type.

SUMMARY OF THE INVENTION

The cultivar 'ESPE2007' has not been observed under all possible environmental conditions and the phenotype may vary somewhat with variations in environment such as temperature, day length, and light intensity, without, however, any variance in genotype. The following traits have been repeatedly observed and are determined to be the unique characteristics of 'ESPE2007'. These characteristics in combination distinguish 'ESPE2007' as a new and distinct *Ficus* cultivar:

1. *Ficus* 'ESPE2007' exhibits a combination of a compact growth habit with a relatively fast rate of growth, making it suitable for production in smaller container sizes, ranging from 14 to 21 centimeters; and
2. *Ficus* 'ESPE2007' exhibits relatively small, elliptic to near-oblong foliage; and
3. *Ficus* 'ESPE2007' exhibits shortened internodal spacing; and
4. *Ficus* 'ESPE2007' exhibits an abundance of prominent and persistent brown stipules present along both the main stem and lateral branches.

BOTANICAL DESCRIPTION OF THE PLANT

Figure 1:
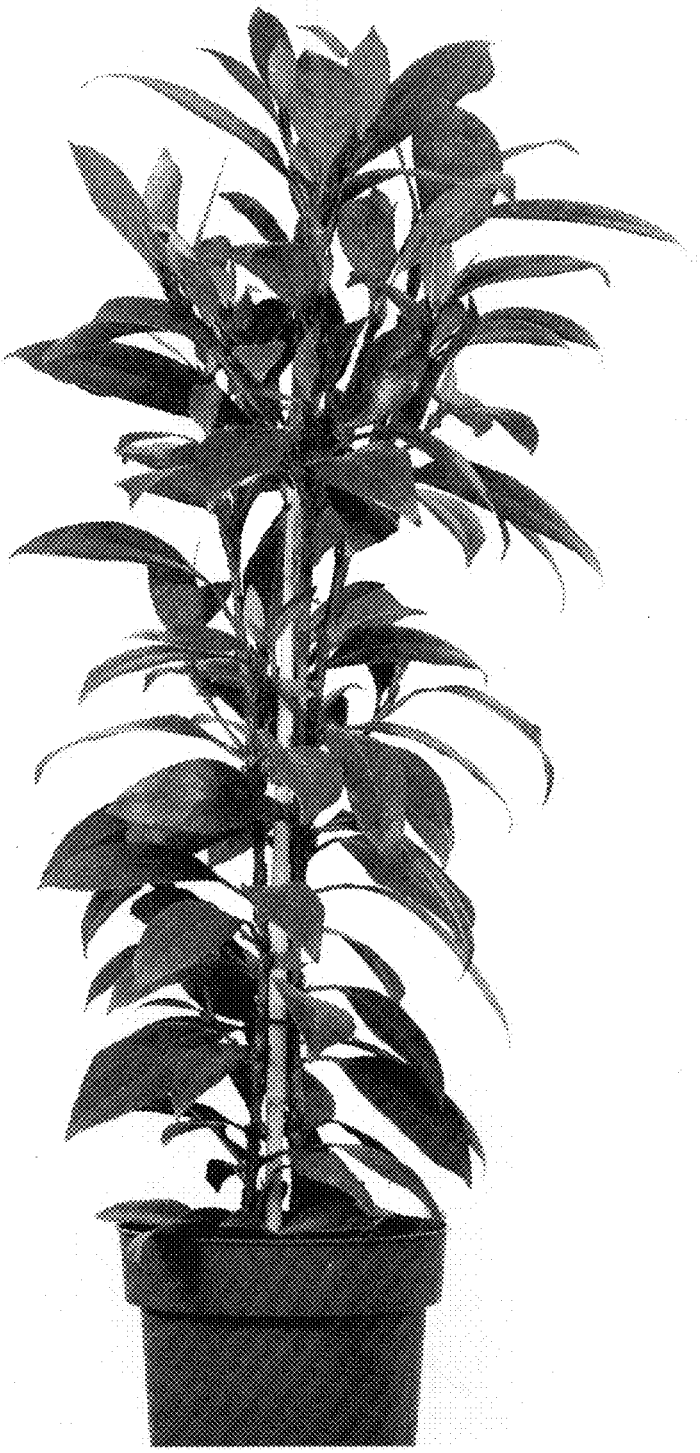
FIG. 1 illustrates, as nearly true as it is reasonably possible to make the same in color photographs of this type, an exemplary plant of 'ESPE2007' grown in a commercial greenhouse ih 's-Gravenzande, the Netherlands. This plant is approximately 25 weeks old, shown planted in a 19 cm container.
Figure 2:
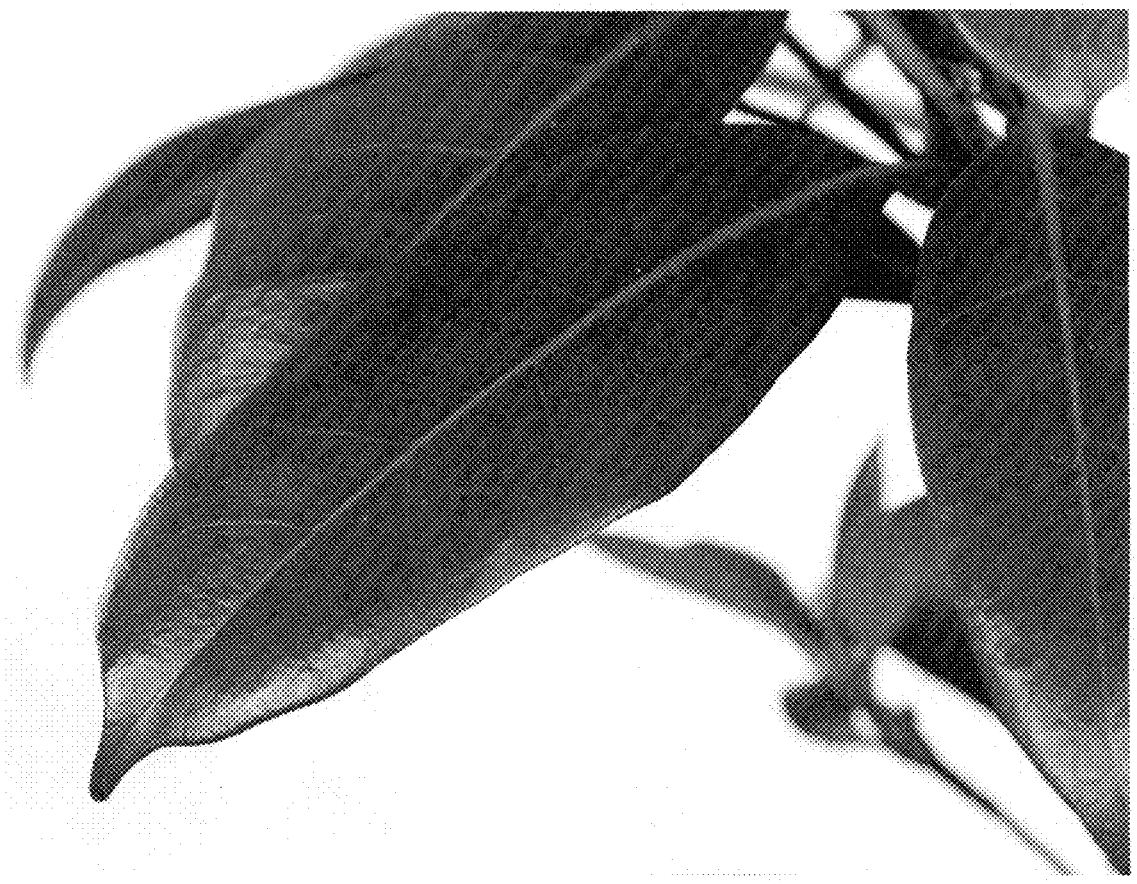
FIG. 2 illustrates, as nearly true as it is reasonably possible to make the same in color photographs of this type, the mature foliage of 'ESPE2007'.
Figure 3:
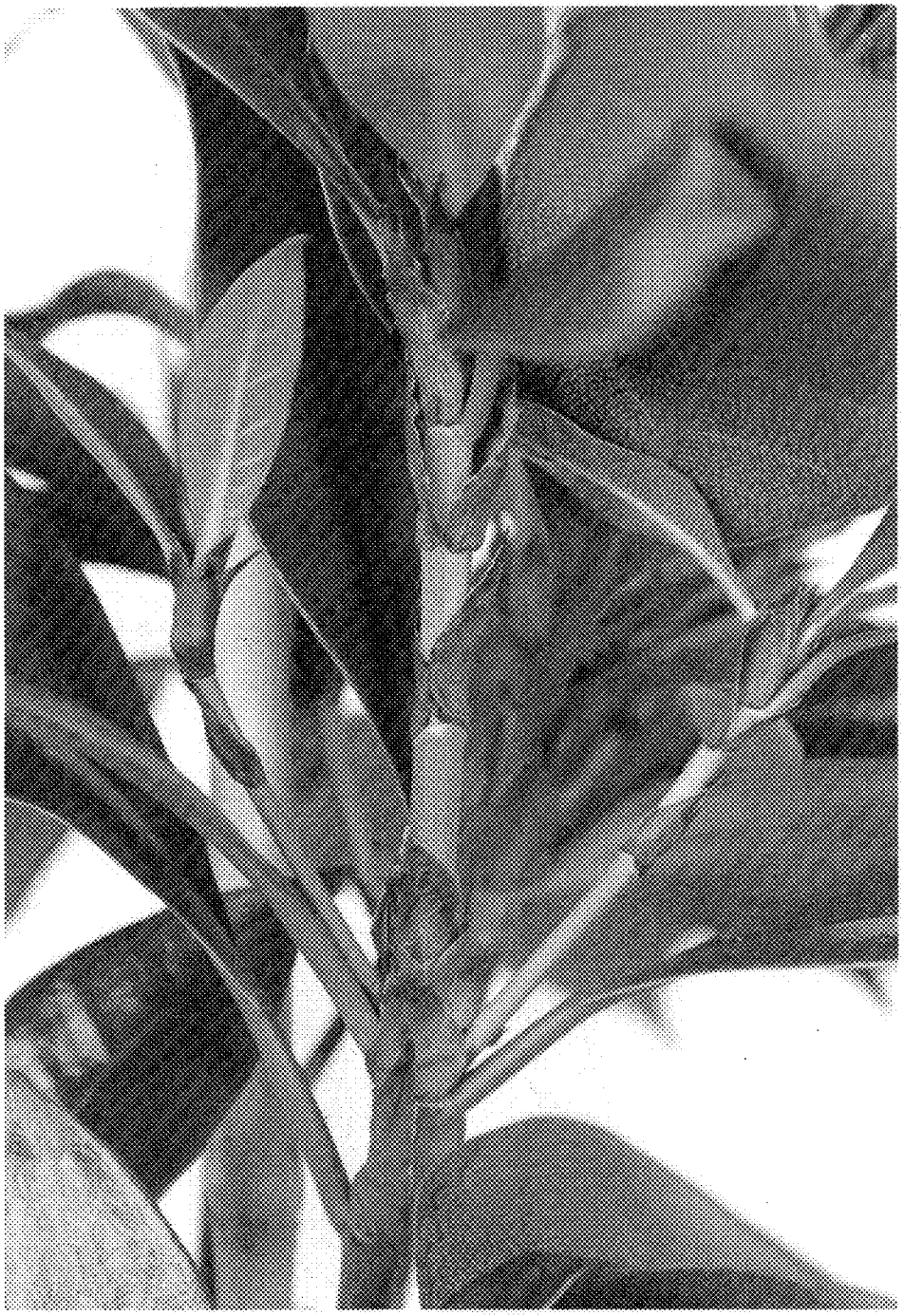
FIG. 3 illustrates, as nearly true as it is reasonably possible to make the same in color photographs of this type, the stems and stipules of 'ESPE2007'.

The following observations and measurements were made in August of 2020 and describe a sample set of six 12 month-old 'ESPE2007' plants grown in 19 cm nursery pots, at a greenhouse in 's-Gravenzande, the Netherlands. Plants were produced in a greenhouse with full sun exposure, ebb and flood irrigation tables, no supplemental fertilizer, and no preventative or pest control measures utilized.

Those skilled in the art will appreciate that certain characteristics will vary with older or, conversely, with younger plants. 'ESPE2007' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on The Royal Horticultural Society Colour Chart, The Royal Horticultural Society, London, 2015 (sixth edition).

A botanical description of 'ESPE2007' and a comparison with the parent plant is provided below.

Plant Description:

*Growth habit.*—Upright.

*Plant form.*—Narrowly obovate to oblong.

*Average height.*—76.8 cm from the soil level to the top of the foliar plane.

*Plant spread.*—Average of 39.8 cm.

*Growth rate.*—Moderately fast to fast.

*Plant vigor.*—Vigorous.

*Propagation type.*—Stem cuttings.

*Time to produce a rooted cutting.*—Approximately 40 days to produce a rooted cutting at approximately 25 degrees Celsius.

*Time to produce a finished plant.*—Approximately 18 weeks to produce a marketable finished plant in a 17 cm pot.

*Disease and pest resistance.*—Neither resistance nor susceptibility to typical *Ficus cyathistipula* pests and diseases has been observed.

*Environmental tolerances.*—Adapt to, at least, USDA Zones 10 through 13 and temperatures as high as 40 degrees Celsius; moderate tolerance to rain; low to moderate tolerance to wind.

Root system:

*General.*—Moderately dense, moderately branched rooting; roots are fibrous.

*Distribution in the soil profile.*—Moderately deep.

*Diameter of roots.*—1.5 mm on average.

*Texture.*—Smooth; no root hairs.

*Color.*—Greyed-orange, nearest to RHS 164B.

Stems and branches:

*General branching habit.*—Multiple main stems, with a plurality of lateral branches; freely branching. Pinching isn't required but will improve branching.

*Main stem.*—Quantity — Three. Length — Approximately 65.7 cm. Diameter — Approximately 0.7 cm. Internode length — Approximately 3.4 cm. Attitude — Near vertical. Aspect — Rounded. Strength — Strong. Texture — Glabrous. Luster — Very slightly glossy. Color, juvenile — Yellow-green, nearest to in between RHS 144A and 144B. Color, mature — Green, nearest to RHS 137B. Color at the leaf nodes — At every node there is a thin radial ring around the stem which is approximately 0.2 cm wide and colored grey-brown, nearest to in between RHS N199C and N199D. Color of the oldest wood — Greyed-brown, RHS N199A.

*Lateral branches.*—Quantity of lateral branches — 16. Attitude — At an angle of approximately 35 degrees to the main stem. Aspect — Rounded. Strength — Strong. Texture — Glabrous. Color, juvenile — Yellow-green, nearest to in between RHS 144A and 144B. Color, mature — Green, nearest to RHS 137B. Color at the leaf nodes — At every node there is a thin radial ring around the branch which is approximately 0.2 cm wide and colored grey-brown, nearest to in between RHS N199C and N199D.

Foliage:

*Arrangement.*—Alternate.

*Division.*—Simple.

*Quantity.*—20 leaves per main stem.

*Attitude.*—Upward and outward.

*Lamina.*—Shape — Elliptic to near-oblong. Aspect — Slightly carinate and very slightly concave. Dimensions — 16.5 cm long and 5.9 cm wide. Apex — Apiculate. Base — Attenuate. Margin — Entire; occasionally slightly repand. Texture of the adaxial surface — Smooth; glabrous. Texture of the abaxial surface — Smooth; glabrous. Luster of the adaxial surface — Moderately glossy. Luster of the abaxial surface — Moderately glossy. Color — Juvenile foliage, adaxial surface — Nearest to a mixture of green and yellow-green, RHS 143A and 146A yet slightly darker. Juvenile foliage, abaxial surface — Yellow-green, nearest to RHS 146B. Mature foliage, adaxial surface — Nearest to a mixture of green and yellow-green, RHS 139A and 147A yet slightly darker; sparsely covered with small, randomly-arranged dots of approximately 1.0 mm in diameter which are colored nearest to in between greyed-purple and black, RHS N186A and 203A. Mature foliage, abaxial surface — Yellow-green, nearest to RHS 144A. Venation — Pattern, adaxial surface — Anastomosing. Pattern, abaxial surface — Anastomosing and reticulate. Color, adaxial surface — Green, nearest to RHS 143A yet slightly darker. Color, abaxial surface — Main vein and secondary veins are yellow-green, nearest to a mixture of RHS 144B and N144A; reticulate veins are green, nearest to RHS NN137B. Petiole — Aspect — Flattened. Length — 2.4 cm. Width — 0.45 cm. Height — 0.4 cm. Strength — Strong. Texture — Smooth; glabrous. Luster — Slightly glossy. Color, adaxial surface — Green, nearest to RHS NN137B. Color, abaxial surface — Nearest to a mixture of green and yellow-green, RHS 138B and 146A. Stipule — General — A single dry stipule is present at the base of each leaf, covering immature leaves before unfolding and persistent at the petiole base of mature leaves. Stipules are very prominent. Shape — Lanceolate to narrowly deltoid. Length — 2.4 cm. Diameter — 1.2 cm. Aspect — Concave. Apex — Acute. Base — Broad cuneate. Margin — Entire; undulate. Texture, adaxial — Smooth; glabrous. Texture, abaxial — Smooth; glabrous. Luster — Matte on both the adaxial and abaxial surfaces. Color, adaxial surface — Grey-brown, nearest to RHS 199D; fading brown towards the apex, RHS 200D. Color, abaxial surface — Brown, RHS 200D; becoming darker towards the apex, RHS 200B.

Inflorescence: No flowering has been observed to date.

Comparison with the parent plant: Plants of the new cultivar 'ESPE2007' differ from the parent, an unnamed *Ficus cyathistipula* plant (not patented), in the following characteristics described in Table 1 below.

TABLE 1

| Characteristic | 'ESPE2007' | The parent |
|---|---|---|
| Growth habit. | Much more compact than the parent. | Much less compact than 'ESPE2007'. |
| Foliage size. | Smaller than the parent. | Larger than 'ESPE2007' |
| Internodal spacing. | Shorter than the parent. | Longer than 'ESPE2007' |

Comparison with the closest known comparator: There are no other named cultivars of *Ficus cyathistipula* known to the inventor. Therefore, the parent is also the most similar commercial comparator known to the inventor.

That which is claimed is:

1. A new and distinct variety of *Ficus cyathistipula* plant named 'ESPE2007', substantially as described and illustrated herein.

* * * * *